United States Patent [19]

Lane

[11] Patent Number: 4,899,013

[45] Date of Patent: Feb. 6, 1990

[54] VISCOUS POLYMERS OF ISOBUTYLENE AND DIENES

[75] Inventor: Kelley R. Lane, Winfield, Ill.

[73] Assignee: Amoco Corporation, Chicago, Ill.

[21] Appl. No.: 260,253

[22] Filed: Oct. 20, 1988

[51] Int. Cl.⁴ ................................................. C07C 2/02
[52] U.S. Cl. ..................................... 585/506; 585/507
[58] Field of Search ................................. 585/506, 507

[56] References Cited

U.S. PATENT DOCUMENTS 3,505,304  4/1970  Davison et al. ...................... 585/506
3,810,952  5/1974  Durand et al. ....................... 585/507

FOREIGN PATENT DOCUMENTS

41/7943  4/1966  Japan .................................... 585/506

Primary Examiner—Curtis R. Davis
Attorney, Agent, or Firm—Matthew R. Hooper; William H. Magidson; Ralph C. Medhurst

[57] ABSTRACT

A process is disclosed for the preparation of copolymers of a diene and isobutylene wherein the copolymer has a degree of unsaturation greater than 100% and average molecular weight range is from 400 to 10,000.

6 Claims, No Drawings

VISCOUS POLYMERS OF ISOBUTYLENE AND DIENES

FIELD OF THE INVENTION

This invention relates to viscous polymers of isobutylene and dienes of average molecular weight of lower than 10,000, usually from about 400 to about 5000, with a degree of unsaturation greater than 100% and with greater reactivity than polymers of polyisobutylene of comparable molecular weight. They are constituted of diolefin and isobutylene units wherein the percent volume mole ratio of diene to isobutylene is from about 1:20 to about 1:3. Their preparation typically requires a Lewis acid-type catalyst, preferably aluminum trichloride. Polymerization temperature is within the range of from about 0° C. to about 40° C., the higher temperatures of 20° C. to about 40° C. resulting in decreased unsaturation, decreased molecular weight, and decreased viscosity of the copolymer. Catalyst concentration is within the range of from about 0.02 wt % to about 0.20 wt %, a lower concentration resulting in a copolymer of increased viscosity and increased unsaturation.

BACKGROUND OR THE INVENTION

Copolymers of isobutylene and diolefins are known and have been widely reported in the prior art. Typically, polymerization processes in which olefinically unsaturated hydrocarbons or mixtures of olefinically unsaturated hydrocarbons are polymerized use Lewis acid-type catalysts. One widely used Lewis acid-type catalyst is an aluminum halide such as aluminum chloride which may be used alone or in the form of a highly active complex with a hydrogen halide such as a hydrogen chloride in an aromatic hydrocarbon such as toluene.

Low molecular weight copolymers of isobutylene and isoprene, of a number average molecular weight of 1000 to 50,000, are taught in U.S. Pat. No. 3,766,155 (Matsushima). Isoolefins taught include isobutylene, 2-methyl-1-butene, 3-methyl-1-butene, 2-methyl-2-butene, 4-methyl-1-pentene, and mixtures thereof as well as styrene, alphamethylstyrene and the like. Examples of multiolefins reacted with isoolefins include isoprene, 1,3-butadiene, 2,3-dimethyl-1,3-butadiene, piperylene, cyclopentadiene, divinylbenzene, cyclohexadiene and the like. The polymerization temperature is generally below 0° C.. The catalyst is a metal organic amide and boron trifluoride.

Other processes for preparation of low molecular weight copolymers of isoprene and isobutylene are known. U.S. Pat. No. 3,562,804 (Powers) teaches a process for preparing low bulk viscosity mastic compositions of isobutylene and isoprene in the presence of a catalyst system comprising an ethyl aluminum dichloride with a halogenated organic promoter, preferably benzyl chloride. Polymerization temperatures range from −30° C. to −80° C. Molecular weights obtained range from 7000 to 81,000, viscosity average molecular weight. The products of this process are characterized by a relatively low degree of unsaturation and find utility in coated and molded articles, mastics, sealants, caulking compounds, etc. Useful polymer compositions of this process include butyl rubber, a high molecular weight solid polymer.

U.S. Pat. No. 3,810/952 (Durand) teaches a method to prepare liquid copolymers of 1,3-butadiene with one or more 1-monoolefins with a high content of unsaturation. The unsaturation is taught as being as high as 96% of the total number of monomeric units which consist of cis-1,4-butadiene units. Average molecular weight by number is less than 40,000 and, in most cases, from 1000 to 5000. The catalyst is a nickel fluorocarboxylate halide. The products are useful as plasticizers, as siccative agents in coatings, as additives for adhesive compositions and as additives for lubricating oils.

A degree of unsaturation greater than 100%, it is to be noted, while desirable for many of the above applications was not attainable by the process of U.S. Pat. No. 3,810,952.

U.S. Pat. No. 4,076,926 (Milner) teaches a method for polymerization of unsaturated compounds wherein the catalyst used is an aluminum trihalide in conjunction with an alcohol or ether. In the absence of the alcohol or ether, a quantity of an undesirable insoluble gel precipitates in the polymerization reactor. Polymerization temperature is in the range of −100° to +200° C., more preferably from 50° C. to 150° C.

Accordingly, despite the desirability of obtaining a copolymer with a degree of unsaturation greater than 100% (see U.S. Pat. 3,810,952) and a copolymer of average molecular weight range of from 400 to 10,000, preferably from 400 to 5000, more preferably from 400 to 1200, suitable for use in polyesters, polyurethanes, polyamines, polyamides, and epoxy resins, the prior art does not disclose a process for preparation of a copolymer with a degree of unsaturation greater than 100%. More than one functional group is required if the resulting copolymer is not to act as an end cap or chain terminator in a specific polymerization in preparation of polyurethanes, polyesters, polyamines and other polymers.

SUMMARY OF THE INVENTION

The present invention is a process for the preparation of unsaturated copolymers of isobutylene and isoprene wherein the copolymer has an unsaturation greater than 100%, an average molecular weight within the range of from 400 to about 10,000, preferably from 400 to 5000, more preferably from 400 to 1200, wherein the catalyst is a Lewis acid-type catalyst, process temperature is from 0° C. to 40° C. and catalyst concentration is from 0.02 wt. % to about 0.20 wt. % of the feedstock.

DETAILS OF THE INVENTION

Isobutylene is copolymerized with a $C_4$ to $C_8$ diene, preferably isoprene. The isobutylene for copolymerization with a $C_4$ to $C_8$ diene can comprise a purified composition of 15-40 wt % isobutylene in an inert gas such as isobutane or n-butane. The isobutylene can also be a product of a catalytic cracker wherein the stream composition is 15-40 wt % isobutylene and the remaining composition comprises olefins including 1-butene, 2-butene and propylene.

Compounds other than isoprene which can be copolymerized with isobutylene by the method of this invention include 1,3-pentadiene, 2,5-dimethyl-1,5-hexadiene, 2,5-dimethyl-2,4-hexadiene or any other $C_4$–$C_8$ diene which is capable of forming an allylic or tertiary cation. Examples are 2-methyl-1,5-hexadiene, 1,3-hexadiene, 1,3-octadiene, 1,3-heptadiene, 2-methyl-1,3-heptadiene and 2-methyl-1,6-hexadiene.

These polymerizations are carried out under Lewis acid-type catalyst conditions, using aluminum chloride as catalyst as an example, at temperatures ranging from 0° C. to about 40° C. The resulting polymers have applications in butyl rubber, unsaturated polyesters, lubricant additives such as detergents and dispersants, and as monomers in other copolymerization reactions.

Unsaturation of the copolymer increases with $C_4$ to $C_8$ olefin content as well as with the amount of vinylidene olefins present. It is therefore essential, for an unsaturation level of greater than 100% in the copolymer, that the ratio of $C_4$ to $C_8$ diene to isobutylene in the copolymerization reaction be in the range of from 1:3 to about 1:20. Quantities of diene added to the copolymerization reaction are from about 5 to 16 mole percent with respect to isobutylene.

Degree of unsaturation is measured by the reactivity of the polymer in m-chloroperbenzoic acid (MCPBA) to produce epoxides or as measured by $^{13}C$ NMR.

MCPBA unsaturation is determined by the reaction of the polymer, dissolved in chloroform, with excess MCPBA for 45 minutes. After reaction the excess MCPBA is reacted with potassium iodide (KI) and the liberated $I_2$ is titrated with sodium thiosulfate. The titer of the MCPBA stock solution, a blank, is determined by processing an aliquot of the stock solution through the same procedure. The amount of MCPBA consumed by the polymer is calculated by difference. From this value and the vapor pressure osmometry (VPO) molecular weight of the polymer, the percent unsaturation is determined.

The $^{13}C$ NmR percent unsaturation is determined by the integrals of olefinic region, 100–150 ppm, and the paraffinic region, 0–65 ppm. These integrals are used to calculate the percent olefinic carbon in the sample. This value is compared to the theoretical percent olefinic carbon calculated from the VPO molecular weight, assuming one olefinic structure per molecule.

The amount of Lewis acid-type catalyst which is used in the polymerization is suitably 0.02 wt % to 0.20 wt %, preferably 0.06 wt % to 0.15 wt %, by weight, when the catalyst is an aluminum halide, based on total feed to be polymerized. The catalyst can be added all at once or in portions during the course of the reaction. While aluminum chloride is preferred as the Lewis acid-type catalyst for reasons of availability, other halides can be used, namely, aluminum iodide or aluminum bromide. Methyl chloride or dichloride can be used with aluminum chloride as a solvent or carrier.

As noted above, the amount of catalyst and the ratio of diene to isobutylene affects the degree of unsaturation of the copolymer. The amount of diene added to the isobutylene is in a volume ratio of from about 1:3 to about 1:20, volume ratio of diene to isobutylene, or about 5 to 16 mole percent with respect to the isobutylene.

The average molecular weights of the said polymers are from 400 to 10,000, preferably from 400 to 5000, most preferably from 400 to 1200, molecular weight units as measured by vapor pressure osmometry (VPO). The VPO method utilizes toluene as the solvent, with benzil being used as a calibration standard. Several standard polybutenes also are used as standards for the method.

The molecular weight distributions of these polymers are defined to have polydispersion indexes between 1.5 and 4.0, being more specific in the range of 1.5 to 2.5 if a narrow molecular weight distribution is preferred for the specific application. The molecular weight distributions, number average molecular weight (Mn), weight average molecular weight (Mw), and the polydispersion indexes (Mw/Mn) are all measured via a gel permeation chromatography (GPC) method. In general the GPC columns are filled with styrene/divinylbenzene copolymer beads of controlled particle and pore size. When polymer molecules are transported through the GPC columns by a solvent, those molecules small enough to penetrate into the pores of the column packings are retarded in their progress through the columns. The molecules which are larger do not or only slightly penetrate into the pore and thus move through the column more rapidly. Therefore, this method separates the polymer based on different sizes of the molecules. To determine the actual molecular weights of the separates polymers standards comprised of fractionated polybutenes are utilized. Based on these standards and the distribution obtained from the columns, the Mn, Mw and D.I. of this invention can be determined.

As was stated previously, this method of polymer preparation allows for both narrow, D.I.<2.5, and broad molecular weight distributions depending on the polymer work up procedure. Broad molecular weight distributions can be advantageous when the highly unsaturated polymers are used as reactive co-monomers in such polymerizations as those to make unsaturated polyesters, polyamides, butyl rubers, etc. The broad molecular weight distributions can enhance compatibility in these systems and thus cause the viscous polymers to be quite reactive. Narrow molecular weight distributions are of interest mainly in petroleum additives where specific properties are desired for dispersants and detergents made from the viscous polymer.

Several aspects of this polymerization must be controlled to allow for tailoring of a highly unsaturated viscous polymer. These are the polymer's unsaturation, >100%, its molecular weight, and its viscosity. In a typical cationic polymerization such as that for isobutylene, temperature and catalyst levels are used to control the viscosity and molecular weight of the polymer. In these polymerizations, temperature also plays an important role. Detailed experiments, Examples VIII and IX, in which the temperature of the reaction was varied, as compared with Example III, revealed the viscosity, VPO molecular weight, and the unsaturation are all dependent upon temperature. That is by varying the temperature form 0° C. to 38° C., the viscosity of the polymer decreases from 400 cSt @ 210° F. to 48 cSt @ 210° F. The VPO molecular weight decreased from 967 to 543 and the MCPBA unsaturation decreased from 150° to 111%. Although it appears that increasing the temperature is detrimental to the degree of unsaturation, this problem has been circumvented by increasing the catalyst level as well as the ratio of isoprene to isobutylene as is shown in Example VI. Under these conditions a low molecular weight, increased unsaturation, viscous polymer has been achieved.

In summary, the instant invention comprises a process for preparation of viscous copolymer of dienes and isobutylene wherein said copolymer has a degree of unsaturation greater than 100% and an average molecular weight range of from 400 to 10,000 wherein said process comprises reacting a feed comprising isobutylene with a $C_4$ to $C_8$ diene in the presence of a catalyst comprising a Lewis acid-type catalyst wherein the volume ratio of $C_4$ to $C_8$ diene to said isobutylene is from 1:3 to about 1:20, at a temperature within the range of from about 0° C. to about 40° C., wherein weight ratio of said catalyst to said feed is from 0.02 wt % to about 0.20 wt %.

In more detail, the instant invention comprises the process as described above wherein said diene is selected from the group consisting of isoprene, 1,3-pentadiene, 2,5-dimethyl-1,5-hexadiene, 2,5-dimethyl-2,4-hexadiene, 2-methyl-1,5-hexadiene, 1,3-hexadiene, 1,3-octadiene, 1,3-heptadiene, 2-methyl-1,3-heptadiene and 2-methyl-1,6-hexadiene, and wherein said Lewis acid-type catalyst is selected from the group consisting of aluminum chloride, aluminum iodide and aluminum bromide.

In still further detail, the instant invention comprises a process, as described above, wherein said diene is isoprene, said catalyst is aluminum chloride and said catalyst to feed weight ratio is from 0.06 wt % to 0.15 wt %, and wherein said viscous copolymer has an average molecular weight range of from 400 to 5000, or wherein said viscous copolymer has an average molecular weight range of from 400 to 1200.

The following examples illustrate the process of the instant invention but are not construed as limiting the scope of the invention.

EXAMPLE I

A 12 oz. Fisher Porter bottle equipped with a magnetic stirrer, a nitrogen inlet, isobutylene inlet, utility inlet and various outlets was used as the reaction vessel. To this vessel 0.137 grams of anhydrous $AlCl_3$ was added along with 10 ml of $CH_2Cl_2$. Then 300 ml of a 20 wt. % isobutylene, 80 wt. % isobutane feed (density=0.557 g/ml) mixed with 7.5 ml (5.1 g) of isoprene were added to the reactor which was maintained at 0° C. by an ice bath. Volume ratio of isoprene to isobutylene was 1:8. The reaction was then carried out for one hour maintaining the temperature of 0° C. After exactly one hour the excess isobutylene and isobutane was vented from the reactor and the reaction quenched by the addition of 50 ml of deionized water. The water killed and removed the $AlCl_3$ catalyst from the polymer. After separation of the water from the polymer, the polymer was dissolved in approximately 50 ml of hexane and dried over anhydrous $MgSO_4$. Next the solvent, hexane, was removed from the polymer via a roto evaporator under conditions of 60° C. and a vacuum of 29 inches of Hg. The combination of five such experiments gave a 65% yield of polymer with respect to isobutylene added to the reactor. Unsaturation by $^{13}C$ NMR was 183%. GPC Mw was 2089. The detailed properties of this polymer including viscosity, molecular weight data and unsaturation data are shown in Table II under Polymer 1.

The above procedure was repeated with volume ratios of isoprene to isobutylene of 1:16 and 1:5.3, and with 1,3-pentadiene, 2,5-dimethyl-1,5-hexadiene and 2,5-dimethyl-2,4-hexadiene. The volume ratio, diene:isobutylene, and percent unsaturation by MCPBA and $^{13}C$ are detailed in Table I.

TABLE I

| Diene | Volume Ratio Diene:Isobutylene | MCPBA % Unsaturation | $^{13}C$ NMR % Unsaturation |
|---|---|---|---|
| Isoprene | 1:16 | 111 | 141 |
| Isoprene | 1:8 | 137 | 183 |
| Isoprene | 1:5.3 | 150 | 207 |
| 1,3-Pentadiene | 1:15.5 | 138 | 139 |
| 2,5-Dimethyl-1,5-hexadiene | 1:16 | 121 | 137 |
| 2,5-Dimethyl-2,4-hexadiene | 1:16 | 161 | 148 |
| None | — | 103 | 113 |

EXAMPLE II

The same experimental procedure was followed as in Example I except for the following changes in reactants: 0.038 grams $AlCl_3$ in 10 ml of $CH_2Cl_2$, 300 ml 20 wt. % isobutylene/80 wt. % isobutane feed, no diene. The polymer properties from this control run are in Table II under Control.

EXAMPLE III

The same experimental procedure was followed as in Example I except for the following changes in reactants: 0.136 grams $AlCl_3$ in 10 ml of $CH_2Cl_2$, 300 ml 20 wt. % isobutylene/80 wt. % isobutane feed mixed with 11.2 ml (7.6 g) of isoprene. This reaction gave a 68% yield of polymer with respect to isobutylene and the properties of the polymer produced are listed in Table II under Polymer 2.

EXAMPLE IV

The same experimental procedure was followed as in Example I except for the following changes in reactants: 0.126 grams $AlCl_3$ in 10 ml of $CH_2Cl_2$, 300 ml 20 wt. % isobutylene/80 wt. % isobutane feed mixed with 5.5 ml (4.1 g) of 2,5-dimethyl-1,5-hexadiene. This reaction gave a 46% yield of polymer with respect to isobutylene and the properties of the polymer are shown in Table II under Polymer 3.

EXAMPLE V

The polymer made from the conditions described in Example III was subjected to a vacuum distillation at 25 inches of Hg and a temperature of 190°-200° C. to remove the low molecular weight material form the polymer. This type of stripping yielded a viscous polymer with a polydispersion index between 1.5 and 2.1 which is similar to the polydispersion index of Indopol Polybutenes (Amoco Corporation, Chicago, Ill.). The properties of this stripped copolymer, Polymer 4, compared to that of a similar molecular weight Indopol Polybutene are shown in Table III. These data show that the unsaturation is increased due to the incorporation of isoprene into the polymer.

TABLE II

Physical Properties of Diene/Isobutylene Copolymers

| Properties | Ex II Control | Ex I Polymer 1 | Ex III Polymer 2 | Ex IV Polymer 3 |
|---|---|---|---|---|
| Diene | none | Isoprene | Isoprene | 2,5-dimethyl-1,5-hexadiene |
| Volume Ratio Diene:Isobutylene | none | 1:8 | 1:5.3 | 1:16 |
| Viscosity 210° F. | 195 cSt | 400 cSt | 400 cSt | 172 cSt |
| VPO Mol. Wt. | 869 | 962 | 967 | 921 |
| GPC Mn | 669 | 583 | 572 | 585 |
| Mw | 2168 | 2089 | 2121 | 1496 |
| Dispersion Index | 3.10 | 3.58 | 3.67 | 2.56 |
| $^{13}C$ NMR % Unsat. | 113 | 183 | 207 | 137 |

TABLE II-continued

Physical Properties of Diene/Isobutylene Copolymers

| Properties | Ex II Control | Ex I Polymer 1 | Ex III Polymer 2 | Ex IV Polymer 3 |
|---|---|---|---|---|
| MCPBA % Unsat. | 103 | 137 | 150 | 121 |

Note:
MCPBA - meta-chloroperbenzoic acid
GPC - Gel permeation chromatography
VPO - Vapor pressure osmometry

TABLE III

Physical Properties of Isoprene/Isobutylene Copolymers after Vacuum Distillation

| Properties | Indopol H-300 Polybutene | Ex V Polymer 4 |
|---|---|---|
| Volume Ratio Isoprene:Isobutylene | none | 1:5.3 |
| Viscosity 210° F. | 665 cSt | 2063 cSt |
| VPO Mn | 1326 | 1324 |
| GPC Mn | 1192 | 1140 |
| Mw | 2029 | 2367 |
| Dispersion Index | 1.70 | 2.08 |
| $^{13}$C NMR & Unsat. | 120 | 171 |
| MCPBA % Unsat. | 95 | 143 |

Note:
VPO Mn - Vapor pressure osmometry average molecular weight

EXAMPLE VI

This example describes the production of a low molecular weight, increased unsaturation viscous polymer. The same procedure was followed as in Example I except for the following changes in reactants and reaction conditions: 0.2020 grams of ALCL$_3$ in 10 ml of CH$_2$Cl$_2$, 300 ml 20 wt % isobutylene/80 wt % isobutane mixed with 20 ml (13.6 g) of isoprene, and a temperature of 38° C. This reaction gave 37% yield with respect to isobutylene. The properties for this polymer were as follows. VPO Mn-681; GPC: Mn-426 Mw-1164, D.I.-2.73; MCPBA unsaturation-166.2%; $^{13}$C NMR unsaturation-202%; Viscosity 210° F.-75 cSt.

EXAMPLE VII

This example describes the production of a low molecular weight, increased unsaturation viscous polymer. The same procedure was followed as in Example I except for the following changes in reactants and reaction conditions: 0.2070 grams of AlCl$_3$ in 10 ml of CH$_2$Cl$_2$, 30 ml 20.4 wt % isobutylene, 0.35 wt % propene, 16.3 wt % 1-butene, and 26.5 wt % 2-butene in inert hydrocarbons mixed with 20 ml (13.6 g) of isoprene, and a temperature of 38° C. This reaction gave 35% yield with respect to isobutylene. The properties for this polymer were as follows: VPO Mn-659; GPC: Mn-441, Mw-1107, D.I.-2.51; MCPBA unsaturation-160.1%; $^{13}$C NMR unsaturation-185%; Viscosity 210° F.-54 cSt.

EXAMPLE VIII

Examples VIII and IX indicate the effect of temperature on molecular weight, unsaturation and product viscosity as compared with the properties of the product of Example III. A higher temperature causes a decrease in molecular weight, unsaturation and product viscosity as compared with the same product properties obtained with a lower temperature.

The same experimental procedure was followed as in Example I except for the following change in reactants and reaction conditions: 0.1361 grams of AlCl$_3$ in 10 ml of CH$_2$Cl$_2$, 300 ml 20 wt. % isobutylene/80 wt. % isobutane mixed with 11.2 ml (7.6 g) of isoprene and a temperature of 21° C. This reaction gave a 88.3% yield with respect to isobutylene. The properties for this polymer are as follows. VPO Mn-727; GPC: MN-515, Mw-1639, D.I.-3.18; MCPBA unsaturation -116%; $^{13}$C NMR unsaturation-114%; Viscosity 210 F.°-124 cSt.

EXAMPLE IX

The same experimental procedure was followed as in Example I except for the following changes in reactants and reaction conditions: 0.1361 grams of AlCl$_3$ in 10 ml of CH$_2$Cl$_2$, 300 ml 20 wt. % isobutylene/80 wt. % isobutane mixed with 11.2 ml (7.6 g) of isoprene and a temperature of 38° C. This reaction gave a 78.3% yield with respect to isobutylene. The properties for this polymer are as follows. VPO Mn-543; GPC: MN-515, Mw-1639, D.I.-3.18; MCPBA unsaturation-111%; $^{13}$C NMR unsaturation-135%; Viscosity 210 F.° -48 cSt.

What is claimed is:

1. A process for preparation of viscous copolymer of dienes and isobutylene wherein said copolymer has a degree of unsaturation greater than 100% and an average molecular weight range of from 400 to 10,000 wherein said process comprises reacting a feed comprising isobutylene with a C$_4$ to C$_8$ diene in the presence of a catalyst comprising a Lewis acid-type catalyst wherein the volume ratio of C$_4$ to C$_8$ diene to said isobutylene is from 1:3 to about 1:20, at a temperature within the range of from about 0° C. to about 40° C., wherein weight ratio of said catalyst to said feed is from 0.02 wt % to about 0.20 wt %.

2. The process of claim 1 wherein said diene is selected from the group consisting of isoprene, 1,3-pentadiene, 2,5-dimethyl-1,5-hexadiene, 2,5-dimethyl-2,4-hexadiene, 2-methyl-1,5-hexadiene, 1,3-hexadiene, 1,3-octadiene, 1,3-heptadiene, 2-methyl-1,3-heptadiene and 2-methyl-1,6-hexadiene.

3. The process of claim 1 wherein said Lewis acid-type catalyst is selected from the group consisting of aluminum chloride, aluminum iodide and aluminum bromide.

4. The process of claim 1 wherein said diene is isoprene, said catalyst is aluminum chloride and said catalyst to feed weight ratio is from 0.06 wt % to 0.15 wt %.

5. The process of claim 1 wherein said viscous copolymer has an average molecular weight range of from 400 to 5000.

6. The process of claim 1 wherein said viscous copolymer has an average molecular weight range of from 400 to 1200.

* * * * *

UNITED STATES PATENT OFFICE
CERTIFICATE OF CORRECTION

Patent No. 4,899,013  Dated February 6, 1990

Inventor(s) Kelley R. Lane

It is certified that error appears in the above-identified patent and that said Letters Patent is hereby corrected as shown below:

Patent reads:

| Col. | Line | | |
|---|---|---|---|
| 4 | 51 | "150°" | and should read --150%-- |
| 7 | 22 | "$^{13}C$ NMR & Unsat." | and should read --$^{13}C$ NMR % Unsat.-- |
| 7 | 34-35 | "isobutane mixed" | and should read --isobutane feed mixed-- |
| 8 | 9-10 | "isobutane mixed" | and should read --isobutane feed mixed-- |

Signed and Sealed this

Sixteenth Day of July, 1991

Attest:

HARRY F. MANBECK, JR.

Attesting Officer  Commissioner of Patents and Trademarks